United States Patent [19]

Arundel et al.

[11] Patent Number: 4,528,986

[45] Date of Patent: Jul. 16, 1985

[54] APPARATUS FOR DETERMINING A DISCOLORED SKIN AREA ON THE SURFACE OF SKIN

[75] Inventors: Philip A. Arundel, Crewe; George B. Horsfall, Macclesfield, both of England

[73] Assignee: Imperial Chemical Industries plc, Great Britain

[21] Appl. No.: 401,392

[22] Filed: Jul. 23, 1982

[30] Foreign Application Priority Data

Aug. 5, 1981 [GB] United Kingdom ............... 8123979

[51] Int. Cl.³ .................................... A61B 5/02
[52] U.S. Cl. .................... 128/665; 128/666; 128/636
[58] Field of Search ............ 128/21, 22, 23, 395, 128/396, 665, 666, 636; 356/425

[56] References Cited

U.S. PATENT DOCUMENTS

| | | | |
|---|---|---|---|
| 2,920,209 | 1/1960 | Asten | 128/666 X |
| 3,562,539 | 2/1971 | Beroza et al. | |
| 3,602,213 | 8/1971 | Howell | 128/666 |
| 3,638,640 | 2/1972 | Shaw | |
| 3,769,974 | 11/1973 | Smart et al. | 128/666 |
| 3,910,701 | 10/1975 | Henderson et al. | |
| 4,015,595 | 4/1977 | Benjamin | 128/666 |
| 4,269,192 | 5/1981 | Matsuo | 128/665 |
| 4,407,290 | 10/1983 | Wilber | 128/665 X |

FOREIGN PATENT DOCUMENTS

| | | | |
|---|---|---|---|
| 0019478 | 11/1980 | European Pat. Off. | 128/665 |
| 2333199 | of 0000 | France | |
| 1527717 | of 0000 | France | |
| 2073879 | of 0000 | United Kingdom | |
| 1386872 | of 0000 | United Kingdom | |
| 2022821 | of 0000 | United Kingdom | |
| 205954A | of 0000 | United Kingdom | |
| 206016A | of 0000 | United Kingdom | |

OTHER PUBLICATIONS

West German OLS No. 1909882 (Battelle Institut E.V.), published Sep. 17, 1970.
Electronic Design, vol. 18, No. 26, Dec. 20, 1970 (Rochelle Park).

Primary Examiner—Edward M. Coven
Attorney, Agent, or Firm—Cushman, Darby & Cushman

[57] ABSTRACT

A novel apparatus and method is disclosed for measuring the reflectance of a colored area of skin in response to green light as a means for assessing the degree of erythema or pigmentation of the area of skin. The apparatus has a mutually screened, green light emitting diode and photosensitive electrical component (typically a cadmium sulphide photoresistor or a silicon photodiode), arranged in a holder and connected to conventional electronic circuitry, so that the amount of light reflected by the area of skin and impinging on the component may be measured and then displayed on a voltmeter allowing a quantitative assessment of erythema or pigmentation. The apparatus has both medical, veterinary and cosmetic applications, for example in assessing the response to treatment of inflammation of the skin, or a safe level of exposure to UV light.

8 Claims, 3 Drawing Figures

APPARATUS FOR DETERMINING A DISCOLORED SKIN AREA ON THE SURFACE OF SKIN

This invention concerns a novel apparatus for measuring reflected light from a coloured area of human, or other warm-blooded animal skin, as a means for assessing the degree of erythema (redness) or pigmentation (especially melanin deposition) of the area of skin.

Various forms of apparatus for quantifying the colour of surfaces by a light reflection technique have been described, for example that described by Dawson et alia, *Phys. Med. Biol.*, 1980, 25, 695–709. These have generally involved the use of high output, incandescent, white light sources, in conjunction with relatively complex lens, filter and light-guide systems for directing light to the surface under investigation and for compensating for fluctuation in the output of the light source. Such apparatuses cannot normally be used outside a laboratory environmemt because of their size, complexity and power requirements and are in general unsuitable for use in the clinical assessment of erythema or pigmentation. The present invention provides a simple, reflected light measuring apparatus which is compact and readily portable and can be used in almost any environment.

According to the invention there is provided an apparatus for measuring the light reflected by a coloured area of skin of a warm-blooded animal, said apparatus comprising a green light emitting diode provided in use with an essentially constant electric current, and a light detector having a photosensitive electric component connected to a conventional circuit for detecting and measuring light induced electrical changes in the photosensitive component, said diode and said photosensitive component being situated and mutually screened within a holder which is generally closed apart from an aperture, so that, in use, substantially all the light received by said photosensitive component is that which has been reflected from the area of skin under investigation, via said aperture and having been emitted by said diode.

The size of the aperture must be such that a sufficiently large area of skin can be examined at any one moment to minimize the effects of minor inconsistencies on the skin surface. For example, for most surfaces an aperture of at least 1 cm$^2$ is required.

The term "mutually screened" is to be understood to mean that the diode and photosensitive component are so situated within the holder that they are physically screened so that the amount of light which passes directly from the diode to the photosensitive component without reflectance from the surface under investigation is negligible. The screening may be a backing piece of the photosensitive component or a separate light-proof screen situated between the diode and photosensitive component.

Although various arrangements of the light emitting diode and photosensitive component relative to the aperture in the holder are possible, a symmetrical arrangement within the holder is generally preferred.

A light guide in the form of a fibre optic, tube or rod, made from a light conducting material such as glass, quartz or perspex, optionally burnished or metallised over its length to prevent loss of light may be used situated between the diode and the aperture of the apparatus in order to concentrate emitted light towards the skin surface. A similar light guide may be interposed between the aperture and the photosensitive component in order to concentrate light reflected from the skin surface. A conventional lens system may also be used for either purpose, but a light guide is generally preferred.

A preferred arrangement is when the diode and photosensitive component are situated coaxially within the holder and centrally disposed relative to the aperture. The aperture itself is conveniently circular.

The holder may be made of any convenient material which is opaque to light, for example sheet metal such as aluminium or an alloy thereof, or opaque plastics material such as nylon, polypropylene or polyvinylchloride.

A particular example of a green light emitting diode, suitable for use in the apparatus is, for example, GaAsP diode such as Farnell No. CM4382B (available from Farnell Electronic Components, Canal Road, Leeds, UK). Similarly the photosensitive component may conveniently be a photoresistor, for example a cadmium sulphide or selenide photoresistor Radiospares No. ORP-12 (available from Radiospares, PO Box 427, 13-17 Epworth Street, London, UK), or a photovoltaic device, for example a silicon or germanium photodiode such as Radiospares No. 308-067 or Centronics No. OSD50-5 (available from Centronics, King Henry's Drive, New Addington, Croydon, Uk).

When a photoresistor is employed, the circuit for measuring light induced changes therein will generally take the form of a conventional resistance measuring arrangement, for example one wherein the photoresistor is connected into one arm of a bridge circuit provided with an essentially constant input voltage so that changes in light intensity reaching the photoresistor are measurable as changes in voltage output across the bridge circuit by means of a voltmeter in conventional manner.

When a photovoltaic device such as a silicon photodiode is employed, increasing light intensity reaching the photodiode causes a change in the short circuit current output therefrom. Accordingly, when such a device is used, the circuit for measuring light induced changes will generally incorporate an operational amplifier whose voltage output is directly related to the current input and may be measured by a conventional voltmeter.

A suitable voltmeter in either case is conveniently of the type providing a digital read-out, for example Lascar NO CBLCM 05R (0-2 volt range) (available from Lascar Electronics, Unit 1, Thomasin Road, Burnt Mills, Basildon, Essex, UK).

The essentially constant electric current for the light emitting diode is necessary to ensure a consistent light output at a given diode temperature and may be provided by any conventional means, for example by an integrated circuit, as shown hereafter in FIG. 3 of the accompanying drawings. A conventional means may also be present for adjusting the current in order to compensate for any decrease in light output of the light emitting diode resulting from a rise in diode temperature.

The power supply for the apparatus will normally be provided by a suitable dry battery but a mains derived supply may also be employed. In general it is preferable to have the power supply and the circuit for measuring light induced electrical changes in the photosensitive component, located remote from the holder, but in miniaturised form they may be incorporated into an extension of the holder.

An advantage of the apparatus is that because a cold light source is employed, essentially no heat is transferred from the holder to the surface under investigation. This is particularly important when the apparatus is being used to measure skin erythema which can vary substantially under the influence of heat. The low weight of the holder is also of advantage for this use since the reflectance properties of skin also vary under the influence of pressure.

In order that the invention may be more readily understood, there will now be described, by way of example, a simple embodiment of the apparatus of the invention with reference to the accompanying drawings in which.

Figure 1:
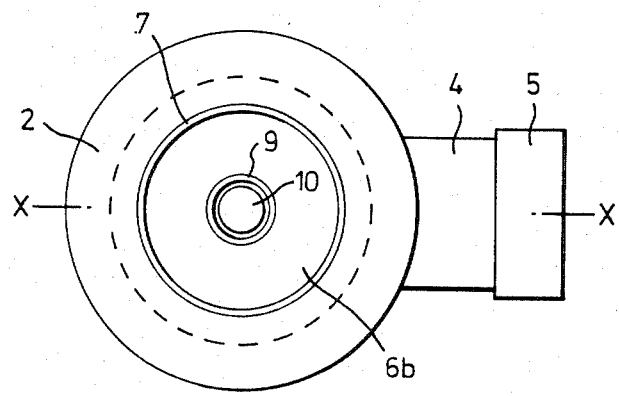
FIG. 1 is an end view of the base of the holder.

The embodiment shown comprises a holder having a generally tubular body (1), a flanged base portion (2) defining an aperture (3), and having a narrower neck portion (4) situated generally at right angles to the body and ending in a collar (5). The holder is conveniently of integral construction from plastics material such as nylon or polyvinylchloride but, as stated above, may be made from any suitable light-proof material.

Within the body (1) of the holder is situated a tubular perspex light guide (6) which has a metal foil (conveniently aluminium foil) coating (7) along its length so that it is a snug fit within the body (1). The guide (6) extends inwardly from the base (2) of the holder away from the aperture (3) towards a photosensitive electrical component (such as a cadmium sulphide photoresistor (8) in the illustrated embodiment), situated towards the middle of the holder. The diameter of the guide (6) and also of the aperture (3) is generally similar to that of the photosensitive electrical component, for example in the range 4-20 mm. The end of the guide (6a) adjacent to the photosensitive electrical component (8) is conveniently recessed to maximise light transmission and to accommodate the convex curvature of the component. Similarly, the end of the guide (6b) adjacent to the aperture is generally recessed conically to allow light passing down the guide to be emitted over the area of the aperture (3). Alternatively, the aperture-proximate end of the guide may be essentially flat, in which case a gap is left between the end of the guide and the aperture.

The inner walls of the guide (6) are also covered by a metal foil coating (9) and define a tubular space within which is situated a light emitting diode (10) with its emitting surface directed towards the aperture-proximate end of the guide (6b). The nonemitting surface of the diode (10) faces towards the photosensitive component but is separated therefrom by a light-proof screening disc (11) through which pass the electrical connections (not shown) to the diode (10).

The collar (5) houses one component of a two component electrical connector (not shown), for example of the male/female type, providing for the necessary electrical connections from a remotely situated power supply and other external electrical circuitry to the diode (10) and the photosensitive component (8). In an alternative arrangement (not shown), the electrical connector may be situated remote from the holder in which case the collar (5) houses a pinch gland to secure the electrical connections as they enter the holder.

Figure 2:
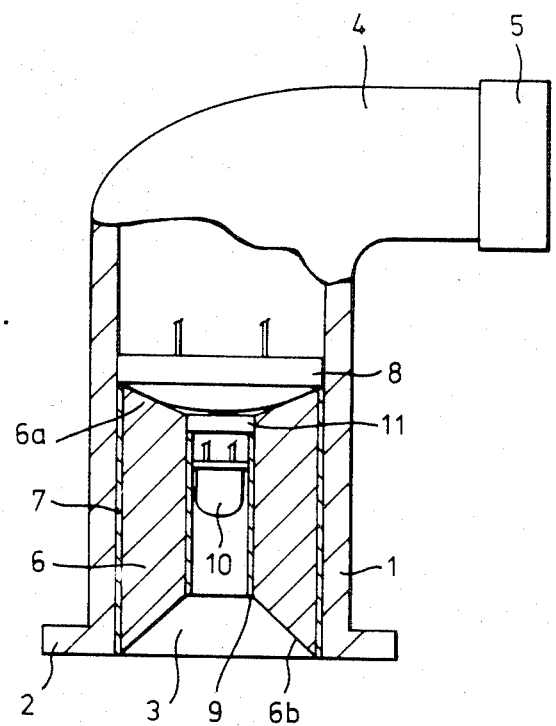
FIG. 2 is a part sectional view of the holder about the line X—X in FIG. 1 and in which, for clarity, the necessary electrical connections are not shown.
Figure 3:
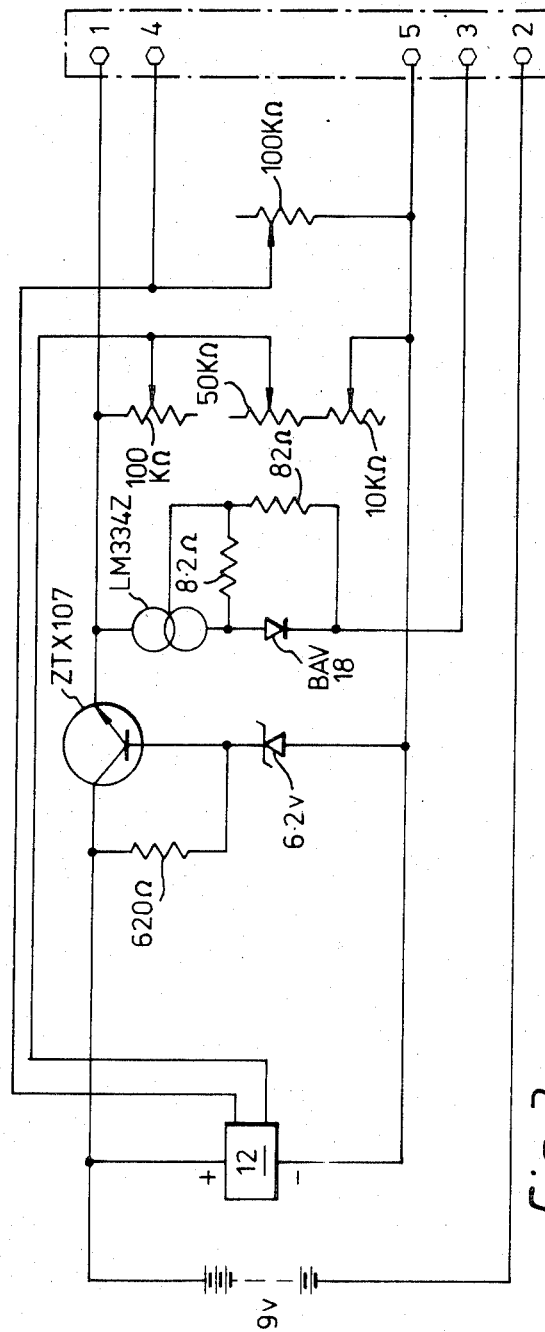
FIG. 3 is a representative electrical circuit diagram for the embodiment.
Figure 3:
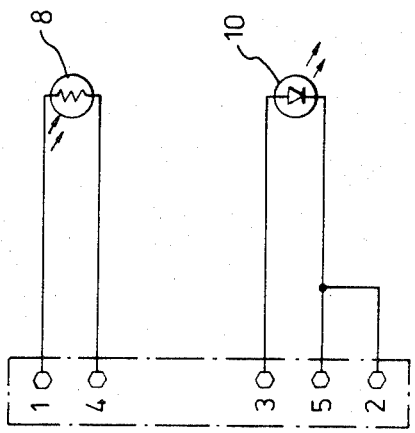

A representative circuit diagram for the particular embodiment of FIGS. 1 and 2 is shown in FIG. 3. The photosensitive component is a cadmium sulphide photoresistor (8) such as Radiospares No ORP 12. The circuit provides a temperature stabilised, constant current via terminals 3 and 5 of one connector component for the light emitting diode (10) such as the GaAsP diode Farnell No. CM 4382B, and a stabilised voltage to a Wheatstone bridge arrangement, one arm of which include via terminals 1 and 4 the photoresistor (8) and the output from which is monitored by a digital read out voltmeter (12) of the liquid crystal display type, such as Lascar No. CB LCM 05R. Terminals 2 and 3 provide an automatic on/off switch for the apparatus.

In use, the two components of the electrical connector are assembled so that electrical connections are made between the remote circuitry and the diode (10) and photoresistor (8) in the holder. The holder is then placed so that the aperture (3) is adjacent to the skin surface under investigation. It is convenient to provide the flanged base position (2) with a soft flexible opaque ring, for example of foam plastics material, in order to minimise the amount of stray light entering the holder as a result of surface irregularities. Light emitted from the diode (10) passes down the tubular space within the guide (6) being reflected from the coating (6b) and then emerges onto and is reflected by the skin surface under investigation via the aperture in the holder. The reflected light is collected by the end of the guide (6b) and transmitted with multiple reflections from the coating (7) to the photoresistor (8). This component decreases in resistance as the intensity of light reaching it increases and causes a consequent change in the voltage across the bridge circuit sensed by the voltmeter (12).

The apparatus may be calibrated by means of a potentionmeter connected in the arm of the bridge circuit opposite that connected to the photoresistor (8). This potentiometer is adjusted to give a fixed voltage reading when the aperture (3) is covered by a black, light-tight end cap. The voltage reading obtained from a white surface such as a barium sulphate card may then be used to give an indication of the maximum reading likely to be obtained.

Alternatively, the embodiment illustrated in FIG. 1 and 2 may be modified by incorporation of a second low output, light emitting diode, which may be switched on when desired to supply a standard amount of light directly (that is without reflectance from the skin surface under investigation) to the photosensitive electrical component.

Time and temperature related changes in the photosensitive component may be compensated for by incorporating a second, essentially identical photosensitive component within the holder. This second photosensitive component would constantly monitor the ouput of the light emitting diode either directly or via a white reflecting surface in the holder. The output from the two photosensitive components would then be compared by conventional electronic means so that a differential value directly related to the reflectance of the skin surface would be applied to the voltmeter (12).

As a still further modificaiton, a conventional filter may be incorporated into the embodiment illustrated in FIG. 1 and 2 situated between the inner end (6a) of the guide (6) and the photosensitive component (8) so that only selected wave lengths of reflected light are detected.

We have discovered that the green light emitted from GaAsP light emitting diodes (that is light of approximately 565 mm wavelength) is particularly suitable for measuring the reflectance of red or brown areas of skin, for example especially those which may be present on skin as a result of local inflammation, burning or melanin pigmentation during tanning. Hitherto the clinical assessment of any reduction in redness (erythema) which may occur during the treatment of inflammation or burning of the skin has generally been carried out subjectively, for example using an arbitrary score of 0 to 5, ranging from no redness to severe inflammation. The assessment is also affected by changes in ambient illumination levels. Similarly, the assessment of a safe level of exposure of areas of skin to UV light, for example for cosmetic, therapeutic or prophylactic purposes, has hitherto also been carried out by largely subjective means. The apparatus of the present invnetion now permits the assessment of the effects of treatment of skin inflammation or the extent of erythema and/or tanning following exposure to UV light to be carried out in a routine manner on a quantitative basis.

The invention accordingly provides a method for assessing the degree of erythema or pigmentation (especially melanin deposition) of an area of skin of a warm-blooded animal (including man) by use of an apparatus as described herein to determine the reflectance of said area of skin in response to green light and in comparison with that of a standard surface. That standard surface may either be the same area of skin at a different point in time, an area of normal skin (i.e. unaffected by erythema or pigmentation) or a standard colour comparison card.

The apparatus is also of value in assessing the effects of various pharmacological agents on skin colour and erythema in laboratory animals during the search for new topical anti-inflammatory or vasoactive agents.

Furthermore, when a photosensitive electrical component with a rapid response to light is used, for example a photovoltaic device such as a silicon photodiode, a range of reflectance values can be obtained as the holder is moved over the skin surface, which can be recorded for example on a pen and chart type voltmeter. This can be of particular value, for example in assessing the progress of skin conditions involving substantial areas of erythema or pigmentation.

An apparatus according to the invention described herein is particularly suitable for assessing erythema or pigmentation of external areas of skin. However, it may readily be modified, for example by use of conventional flexible, coaxial fibre optic light guides, to make it suitable for examining the reflectance of internal areas of skin, for example in the mouth or throat as a means for assessing inflammation of these areas, for example in assessing inflammation of the gums (gingivitis) or tonsils (tonsilitis).

It will be appreciated that an apparatus according to the invention can also be used in other applications where a portable or miniaturised apparatus for assessing the reflectance of a surface in response to green light is required, for example in the routine assessment of the degree of ripening of fruits such as apples, oranges or bananas.

What we claim is:

1. Apparatus for determining a discolored skin area on the surface of the skin of a warm-blooded animal by detecting and measuring the intensity of light reflected from the skin surface, said apparatus comprising:

a body member defining a generally tubular interior space and including means establishing a base surface for placement against the skin surface, said interior space at said base surface thereby defining a circular illumination area;

light detector means including a photosensitive element disposed in said interior space of said housing so as to be in spaced-apart relationship relative to said illumination area, said light detector means for detecting and measuring light reflected from said illumination area;

annular light guide means for guiding light reflected from said illumination area towards said photosensitive element, said light guide means having upper and lower ends and disposed in said interior space so that said upper and lower ends are adjacent said photosensitive element and said illumination area, respectively, said light guide means including an outer shield wall adjacent said body member and an inner shield wall defining a tubular inner aperture coaxially disposed relative to said interior space, said light guide means at said lower end including means defining a recessed surface located adjacent to but spaced above said skin surface between said outer shield wall and said inner shield wall;

light emitting means coaxially disposed in said inner aperture and having a light emitting element in confronting relationship to and spaced above said skin surface, said light emitting means for emitting a steady light, said emitted light being shielded from direct impingement upon said light guide means by said inner shield wall thereby being guided to said skin surface in said illumination area, said emitted light guided to said skin surface in said illumination area being reflected by said skin surface in said illumination area so as to impinge upon said recessed surface of said lower end of said light guide means and subsequently guided by said light guide means to said photosensitive element to be detected and measured by said light detector means, the intensity of said detected and measured light being indicative of a discolored skin area in said illumination area; and light shield means disposed in said inner aperture between said photosensitive element and said light emitting means for preventing said photosensitive element from sensing light emitted by said light emitting element in said inner aperture thereby ensuring that said photosensitive element senses substantially all light reflected from the skin surface in said illumination area.

2. An apparatus as claimed in claim 1 wherein said light emitting means includes a gallium arsenide phosphide diode and said photosensitive component is selected from a photoresistor and a photovoltaic device.

3. An apparatus as claimed in claim 2 wherein said light detector means comprises a cadmium sulphide photoresistor, connected into one arm of a conventional bridge circuit, and a voltmeter, said circuit provided in use with an essentially constant input voltage, whereby changes in light intensity reaching said photoresistor are measurable as changes in output voltage across the bridge by means of said voltmeter.

4. An apparatus as claimed in claim 2 wherein the light detector means comprises a silicon photodiode as photovoltaic device connected via an operational amplifier to a voltmeter whereby, in use, changes in light intensity reaching said photodiode cause a change in the short circuit current output therefrom, which output is fed to said amplifier whose voltage output is measured by means of said voltmeter.

5. Apparatus as in claim 1 wherein said light guide means includes means defining a second recessed surface at said upper end.

6. Apparatus as in claim 5 wherein said recessed surface defined at said upper end is a concave surface.

7. Apparatus as in claim 1 wherein said recessed surface defined at said lower end is conically shaped.

8. Apparatus as in claim 1 wherein said inner and outer shield walls of said light guide means are coated with metal foil means for reflecting light.

* * * * *